United States Patent [19]
Johnson et al.

[11] Patent Number: 5,494,887
[45] Date of Patent: Feb. 27, 1996

[54] RING ANNULATED 5-ALKOXY-N-ARYL[1,2,4]TRIAZOLO[1,5-C]-PYRIMIDINE-2-SULFONAMIDE HERBICIDES

[75] Inventors: Timothy C. Johnson; Walter Reifschneider; John C. Van Heertum; Mark J. Costales; Kim E. Arndt, all of Indianapolis, Ind.

[73] Assignee: DowElanco, Indianapolis, Ind.

[21] Appl. No.: 273,522

[22] Filed: Jul. 11, 1994

[51] Int. Cl.⁶ ........................................... A01N 43/54
[52] U.S. Cl. ................... 504/241; 544/251; 546/297; 546/304
[58] Field of Search ..................... 504/241; 544/251

[56] References Cited

U.S. PATENT DOCUMENTS

| | | | |
|---|---|---|---|
| 4,638,075 | 1/1987 | Kleschick | 544/251 |
| 4,818,273 | 4/1989 | Kleschick et al. | 544/263 |
| 4,872,901 | 10/1989 | Aoki et al. | 544/255 |
| 5,071,468 | 12/1991 | Astles et al. | 504/241 |
| 5,163,995 | 11/1992 | Van Heertum et al. | 544/263 |
| 5,201,938 | 4/1993 | Costales et al. | 544/263 |
| 5,217,521 | 6/1993 | Durr et al. | 504/241 |

FOREIGN PATENT DOCUMENTS

| | | |
|---|---|---|
| 217748 | 4/1987 | European Pat. Off. . |
| 244948 | 11/1987 | European Pat. Off. . |
| 419831 | 8/1990 | European Pat. Off. . |

*Primary Examiner*—Donald G. Daus
*Attorney, Agent, or Firm*—D. Wendell Osborne

[57] ABSTRACT

Substituted ring annulated 5-alkoxy-N-aryl-[1,2,4]triazolo[1,5-c]pyrimidine-2-sulfonamide compounds, such as N-(2,6-dichlorophenyl)-5-methoxycyclopenteno[d]-[1,2,4]triazolo[1,5-c]pyrimidine-2-sulfonamide, were prepared by condensation of an appropriate 2-chloro-sulfonyl-5-alkoxy[1,2,4]triazolo[1,5-c]pyrimidine compound, such as 2-chlorosulfonyl-5-methoxycyclopenteno[d][1,2,4]triazolo[1,5-c]pyrimidine, with a substituted arylamine compound, such as 2,6-dichloroaniline, and found to possess herbicidal utility.

22 Claims, No Drawings

RING ANNULATED 5-ALKOXY-N-ARYL[1,2,4] TRIAZOLO[1,5-C]-PYRIMIDINE-2-SULFONAMIDE HERBICIDES

BACKGROUND OF THE INVENTION

The present invention relates to substituted sulfonamide compounds, to herbicidal compositions containing the compounds, and to the utility of the compounds for the control of unwanted vegetation.

The control of unwanted vegetation by means of chemical agents, i.e., herbicides, is an important aspect of modern agriculture and land management. While many chemicals that are useful for the control of unwanted vegetation are known, new compounds that are more effective generally, are more effective for specific plant species, are less damaging to desirable vegetation, are safer to man or the environment, are less expensive to use, or have other advantageous attributes are desirable.

A number of sulfonamide compounds, including certain substituted [1,2,4]triazolo[1,5-a]pyrimidine-2-sulfonamide compounds (U.S. Pat. No. 4,954,163) and [1,2,4]triazolo[1,5-c]pyrimidine-2-sulfonamide compounds (U.S. Pat. No. 5,010,195 and European Application 244,948), are known and are known to possess herbicidal activity, especially on broadleaf weeds.

SUMMARY OF THE INVENTION

It has now been found that certain ring annulated 5-alkoxy-N-aryl[1,2,4]triazolo[1,5-c]pyrimidine-2-sulfonamide compounds are potent herbicides for the control of unwanted vegetations have desirable crop selectivity, and have favorable toxicological and environmental attributes.

The invention includes 5-alkoxy-N-aryl[1,2,4]triazolo[1,5-c]pyrimidine-2-sulfonamide compounds of Formula I:

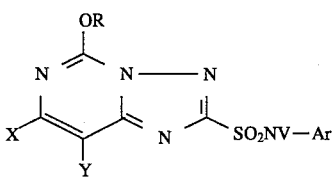

wherein

R represents $CH_2CF_3$ or $(C_1-C_3)$alkyl optionally monosubstituted with F, Cl, or $OCH_3$;

X and Y together represent a biradical fragment of the formula —Z—CH=CH—, —CH=CH—Z—, —Z—$CH_2$—$CH_2$—, —$CH_2$—$CH_2$—Z—, —$(CH_2)_3$—, —CH=CH—CH=CH—, or —N=CH—CH=CH— each optionally substituted with $CH_3$;

Z represents O, S, or $NCH_3$;

V represents H, COR', COR', $CO_2R''$, or $CONR'''2$;

Ar represents an aromatic moiety one of the formulas:

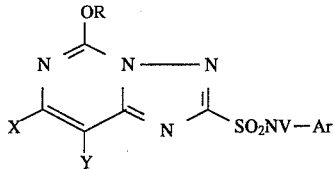

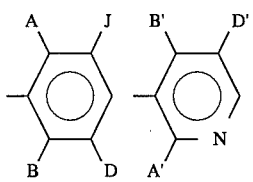

A represents F, Cl, Br, $CO_2R''$, $CONR'''2$, $(C_1-C_2)$haloalkyl, $NO_2$, CN, SOR', or $SO_2R'$;

B represents H, $CH_3$, $C_2H_5$, F, Cl, Br, CN, OR', SR', $NR'''2$, phenyl, or phenoxy, each phenyl and phenoxy optionally possessing 1 to 3 substituents selected from the group consisting of F, Cl, Br, CN, $CF_3$, $NO_2$, and $CH_3$;

D and J each independently represents H or $CH_3$ with the proviso that at least one of D and J represents H;

A' and B' each independently represents H, R', OR', $S(O)_nR'$, F, Cl, Br, I, CN, $NO_2$, $C_6H_5$, $CO_2R''$, or $CONR'''2$ with the proviso that not more than one of A' and B' represents H;

D' represents H, F, Cl, Br, I, $CF_3$, or $CH_3$;

A" represents F, Cl, Br, I, $CF_3$, $SCF_3$, CN, $CO_2R''$, or $CONR'''2$ and is located in the 4-position when the point of attachment is the 3- or 5-position and represents F, Cl, Br, I, $CF_3$, or $CH_3$ and is located in the 3- and/or 5-position when the point of attachment is the 4-position;

T represents H or F;

n represents 0, 1, or 2;

R' represents $(C_1-C_4)$alkyl optionally singly to completely substituted with fluorine;

R" represents $(C_1-C_4)$ alkyl, $(C_3-C_4)$ alkenyl, or $(C_3-C_4)$ alkynyl;

R'" represents H or $(C_1-C_4)$alkyl; and when V represents H, the agriculturally acceptable salts thereof.

The compounds of the invention, usually in the form of an herbicidal composition containing one or more of them in admixture with an agriculturally acceptable adjuvant or carrier, exhibit strong herbicidal properties when applied either directly to the unwanted vegetation or to the locus thereof and when applied either preemergence or postemergence.

DETAILED DESCRIPTION OF THE INVENTION

The herbicidal compounds of the invention are ring annulated 5-alkoxy-N-aryl[1,2,4]triazolo[1,5-c]-pyrimidine- 2-sulfonamide compounds of Formula I:

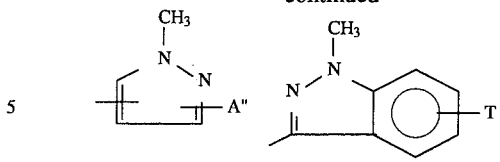

These compounds can be described as amides derived from ring annulated 5-alkoxy-N-aryl[1,2,4]triazolo[1,5-c]-pyrimidine- 2-sulfonic acid compounds and substituted aromatic amine compounds. Each of these compounds possess a biradical substituent on the [1,2,4]triazolo[1,5-c]-pyrimidine nucleus, which radical creates an annulated ring.

The compounds of the invention include compounds of Formula I wherein X and Y together represent an optionally substituted biradical fragment of the formula —O—CH=CH—, —CH=CH—O—, —S—CH=CH—, —CH=CH—S—, —(CH$_3$)N—CH=CH—, —CH=CH—N(CH$_3$)—, —O—CH$_2$—CH$_2$—, —CH$_2$—CH$_2$—O—, —S—CH$_2$—CH$_2$—, —CH$_2$—CH$_2$—S—, —(CH$_3$)N—CH$_2$—CH$_2$—, —CH$_2$—CH$_2$—N(CH$_3$)—, —(CH$_2$)$_3$—, —CH=CH—CH=CH—, or —N=CH—CH=CH—, each of which may be substituted with a methyl group. In the foregoing and throughout this document, the left side bond of the biradical is, by convention, attached at the X-position and the right side bond is attached at the Y-position. The biradical fragments —CH=CH—S— and —(CH$_2$)$_3$—, which result in ring annulated 5-alkoxy-N-aryl[1,2,4]triazolo-[1,5-c]pyrimidine-2-sulfonamide compounds of the formulas:

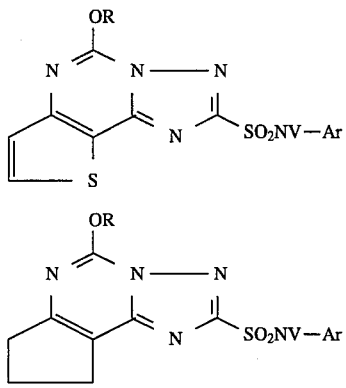

are often preferred.

The compounds of the invention include those of Formula I wherein R represents (C$_1$–C$_3$)alkyl optionally monosubstituted with fluoro, chloro or methoxy or represents 2,2,2-trifluoroethyl. Compounds wherein R represents methyl or ethyl are usually preferred.

The compounds of the invention further include those wherein V represents hydrogen, an acyl moiety, a hydrocarbyloxycarbonyl, or a carbamoyl moiety. Such compounds wherein V represents H, COR', CO$_2$R'', or CONR'''2 and R' represents (C$_1$–C$_4$)alkyl optionally singly to completely substituted with fluorine, R'' represents (C$_1$–C$_4$)alkyl, (C$_3$–C$_4$)alkenyl, or (C$_3$–C$_4$)alkynyl, and R''' represents H or (C$_1$–C$_4$)alkyl are specifically identified. When V represents hydrogen, the compounds of Formula I are acidic and the invention includes the agriculturally acceptable salts of these acids. Compounds of Formula I wherein V represents hydrogen are generally preferred.

The term Ar in Formula I represents an aromatic moiety, especially an aromatic moiety of one of the following formulas:

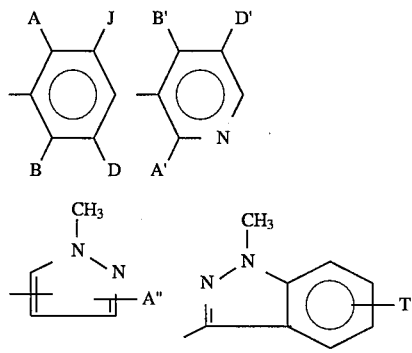

which includes phenyl moieties, 3-pyridinyl moieties, 1-methyl-(3-, 4-, or 5-)pyrazolyl moieties, and 1-methyl-3-indazolyl moieties.

When Ar represents a phenyl moiety, the moiety is substituted in at least one ortho position with an electron withdrawing group. Compounds of Formula I wherein Ar represents a substituted phenyl moiety include those wherein A represents F, Cl, Br, CO$_2$R'', CONR'''2, (C$_1$–C$_2$)haloalkyl, NO$_2$, CN, SOR', or SO$_2$R'; B represents H, CH$_3$, C$_2$H$_5$, F, Cl, Br, CN, OR', SR', NR'''2, phenyl, or phenoxy, each phenyl and phenoxy optionally possessing 1 to 3 substituents selected from the group consisting of F, Cl, Br, CN, CF$_3$, NO$_2$, and CH$_3$; and D and J each independently represents H or CH$_3$ with the proviso that at least one of D and J represents H. Compounds wherein A represents one of F, Cl, Br, CO$_2$R'', NO$_2$, and CF$_3$; B represents one of F, Cl, Br, OCH$_3$, and CH$_3$; J represents H, and D represents H or CH$_3$ are often preferred. Compounds wherein A and B both represent F or Cl and D and J both represent H; wherein A and B both represent F or Cl, D represents CH$_3$, and J represents H; wherein A represents CO$_2$CH$_3$, B represents Cl or F, and D and J both represent H; and wherein A represents CF$_3$, B represents OCH$_3$, and D and J both represent H are often more preferred. Compounds wherein A represents F, Cl, or CO$_2$CH$_3$, B represents F or Cl, and D and J each represent H are sometimes especially preferred.

When Ar represents a 3-pyridinyl moiety, the moiety is substituted in at least one of the 2- and 4-positions. Compounds that are substituted in both of these positions are often preferred. Compounds of Formula I wherein Ar represents a substituted 3-pyridinyl moiety include those wherein A' and B' are selected from H, F, Cl, Br, I, CN, NO$_2$, C$_6$H$_5$, CO$_2$R'', or CONR'''2, or (C$_1$–C$_4$)alkyl, (C$_1$–C$_4$)alkoxy, (C$_1$–C$_4$)alkylthio, (C$_1$–C$_4$)alkylsulfinyl, or (C$_1$–C$_4$)-alkylsulfonyl, each optionally singly to completely substituted with fluorine, and D' represents H, F, Cl, Br, I, CF$_3$, or CH$_3$. Compounds wherein A' and B' each independently represents H, CH$_3$, C$_2$H$_5$, O(C$_1$–C$_3$)alkyl, F, Cl, Br, or CO$_2$(C$_1$–C$_3$)-alkyl with the proviso that not more than one of A' and B' represents H; and D' represents H or CH$_3$ are often preferred. Such compounds wherein A' represents Cl, F, or OCH$_3$; B' represents CH$_3$, OCH$_3$, OC$_2$H$_5$, OC$_3$H$_7$(n), or OC$_3$H$_7$(i); and D' represents H or wherein A' represents H, B' represents CO$_2$(C$_1$–C$_2$)alkyl and D' represents H are typically more preferred. 3-Pyridinyl moieties wherein A' represents F, B' represents CH$_3$, and D' represents H and wherein A' represents Cl, B' represents OCH$_3$ or OC$_2$H$_5$, and D' represents H are sometimes more preferred.

When Ar represents a pyrazolyl moiety, the moiety is attached to the sulfonamide nitrogen atom at a 3-, 4-, or 5-position and has a methyl group in the 1-position. When the point of attachment is the 3- or 5-position, the moiety is substituted in the 4-position with an electron withdrawing group. The 3- or 5-position attachment compounds wherein the 4-position substituent A'' represents F, Cl, Br, I, CF$_3$, SCF$_3$, CN, CO$_2$R'', or CONR'''2 are specifically identified. Those wherein A'' represents Cl, Br, I, or CF$_3$ are usually more preferred. When the point of attachment is the 4-position, the moiety is substituted in the 3- and/or 5-position. Such compounds wherein the 3- or 5-position substituent A'' represents F, Cl, Br, I, CF$_3$, or CH$_3$ are specifically identified. Those wherein A'' represents Cl, Br, I, or CF$_3$ are usually more preferred.

When Ar represents an indazolyl moiety, the moiety is attached to the sulfonamide nitrogen atom at the 3-position, has a methyl group in the 1-position, and is optionally mono-substituted with fluorine. Such compounds having a fluoro substituent in the 4-position are often preferred.

The term alkyl as used herein includes straight chain, branched chain, and cyclic moieties. Thus, typical alkyl groups are methyl, ethyl, 1-methylethyl, propyl, cyclopropyl and the like. Methyl and ethyl are often preferred. Typical alkyl groups singly to completely substituted with fluorine include trifluoromethyl, monofluoromethyl, 2,2,2-trifluoroethyl, 2,3-difluoropropyl, and the like; trifluoromethyl is often preferred. The term haloalkyl is used herein to denote alkyl singly to completely substituted with fluorine or chlorine and includes trifluoromethyl, dichloromethyl, 2,2-difluoro-2-chloroethyl, and the like; trifluoromethyl is often preferred.

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula:

$$R^6R^7R^8NH^\oplus$$

wherein $R^6$, $R^7$, and $R^8$ each, independently represents hydrogen or $(C_1-C_{12})$alkyl, $(C_3-C_{12})$cycloalkyl, or $(C_3-C_{12})$alkenyl, each of which is optionally substituted by one or more hydroxy, $(C_1-C_8)$alkoxy, $(C_1-C_8)$alkylthio or phenyl groups; provided that $R^6$, $R^7$, and $R^8$ are sterically compatible. Additionally, any two of $R^6$, $R^7$, and $R^8$ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

While each of the ring annulated 5-alkoxy-N-aryl[1,2,4]triazolo[1,5-c]pyrimidine-2-sulfonamide compounds encompassed by Formula I is within the scope of the invention, the degree of herbicidal activity and the spectrum of weed control obtained varies depending upon the substituents present.

A listing of some typical compounds of the invention is given in Table 1. Some of the specifically preferred compounds of the invention include the following: N-(2,6-dichlorophenyl)-5-methoxycyclopenteno[d][1,2,4] triazolo[1,5-c]pyrimidine-2-sulfonamide, N-(2,6-dichlorophenyl)-5-methoxythieno[3,2-e] [1,2,4] triazolo [1,5-c] pyrimidine and N-(2,6-dichlorophenyl)-5-methoxypyrido-[3,2-e] [1,2,4] triazolo[1,5-c]pyrimidine-2-sulfonamide.

TABLE 1

N-ARYL[1,2,4]TRIAZOLO[1,5-C]PYRIMIDINE-2-SULFONAMIDE COMPOUNDS

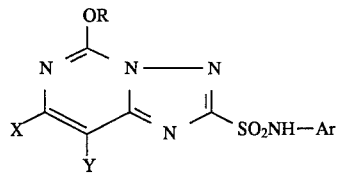

| Cpd. No. | R | XY | Ar | Form | Melting point, °C. | % C calc. found | % H calc. found | % N calc. found | % S calc. found |
|---|---|---|---|---|---|---|---|---|---|
| 1 | $CH_3$ | —CH=CH—CH=CH— | 2,6-difluorophenyl | white powder | 226–227 (dec) | 49.1 48.9 | 2.83 2.76 | 17.9 18.0 | 8.19 7.90 |
| 2 | $CH_3$ | —CH=CH—CH=CH— | 2,6-dichlorophenyl | white powder | 242–243 (dec) | 45.3 45.1 | 2.61 2.71 | 16.5 16.4 | 7.56 7.59 |
| 3 | $CH_3$ | —CH=CH—CH=CH— | 1-methyl-4-bromo-3-pyrazolyl | tan powder | >240 | 38.4 38.7 | 2.76 2.83 | 22.4 22.6 | 7.32 7.03 |
| 4 | $CH_3$ | —N=CH—CH=CH— | 2,6-dichlorophenyl | tan powder | 290–293 (dec) | 42.4 42.6 | 2.37 2.58 | 19.8 18.7 | 7.54 7.44 |
| 5 | $CH_3$ | —N=CH—CH=CH— | 2,6-dichlorophenyl | tan powder | 292–295 (dec) | 45.9 46.4 | 2.57 2.76 | 21.4 20.5 | 8.17 8.07 |
| 6 | $CH_3$ | —CH=CH—S— | 2,6-dichlorophenyl | white powder | 224–226 | 39.1 39.4 | 2.11 2.16 | 16.3 16.2 | 14.9 15.0 |
| 7 | $CH_3$ | —CH=CH—S— | 2-fluoro-6-methoxy-carbonylphenyl | yellow powder | 203–206 | 43.9 44.2 | 2.77 2.87 | 16.0 16.0 | 14.8 14.8 |
| 8 | $CH_3$ | —CH=CH—S— | 2-fluoro-4-methyl 3-pyridinyl | tan solid | 183–185 (dec) | 47.6 47.4 | 4.00 3.97 | 22.2 21.8 | |
| 9 | $CH_3$ | —CH=CH—S— | 1-methyl-4-bromo-3-pyrazolyl | tan powder | 243 (dec) | 32.4 32.1 | 2.27 2.15 | 22.1 21.8 | 14.3 14.2 |
| 10 | $CH_3$ | —C(CH_3)=CH—S— | 2,6-dichlorophenyl | tan powder | 221–224 (dec) | 40.6 42.8 | 2.50 3.71 | 15.76 15.65 | 14.4 13.5 |
| 11 | $CH_3$ | —CCl=C(CH_3)—S— | 2,6-dichlorophenyl | tan powder | 207–209 (dec) | 37.6 37.0 | 2.11 2.19 | 14.6 13.8 | 13.4 12.9 |
| 12 | $CH_3$ | —CH_2CH_2CH_2— | 2,6-dichlorophenyl | tan powder | 211–213 (dec) | 43.5 43.8 | 3.16 3.21 | 16.9 16.5 | 7.74 7.69 |
| 13 | $CH_3$ | —CH_2CH_2CH_2— | 2,6-dichlorophenyl | tan powder | 198–200 | 47.2 46.1 | 3.44 3.56 | 18.4 17.3 | 8.41 7.72 |
| 14 | $CH_3$ | —CH_2CH_2CH_2— | 2-chloro-6-methoxy-carbonylphenyl | tan powder | 204–206 | 46.6 46.5 | 3.68 3.84 | 16.0 15.9 | 7.32 7.18 |
| 15 | $CH_3$ | —CH_2CH_2CH_2— | 2,6-dichloro-3- | tan | 188–191 | 44.9 | 3.53 | 16.4 | 7.49 |

TABLE 1-continued

N-ARYL[1,2,4]TRIAZOLO[1,5-C]PYRIMIDINE-2-SULFONAMIDE COMPOUNDS

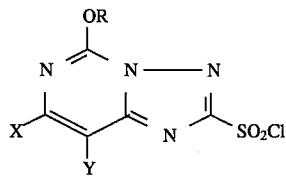

| Cpd. No. | R | XY | Ar | Form | Melting point, °C. | % C calc. found | % H calc. found | % N calc. found | % S calc. found |
|---|---|---|---|---|---|---|---|---|---|
| | | | methylphenyl | powder | (dec) | 45.1 | 3.99 | 16.3 | 7.74 |
| 16 | CH₃ | —CH₂CH₂CH₂— | 4-fluoro-1methyl-3-indazolyl | tan powder | 221–222 | 48.9 48.7 | 3.86 3.97 | 23.5 23.1 | 7.68 7.31 |
| 17 | CH₃ | —CH₂CH₂CH₂— | 2-fluoro-4-methyl-3-pyridinyl | white flakes | 272–274 (dec) | 42.6 42.5 | 2.81 2.67 | 21.3 21.0 | |
| 18 | C₂H₅ | —OCH₂CH₂— | 1-methyl-4-bromo-5-pyrazolyl | | | | | | |

The compounds of Formula I wherein V represents hydrogen can generally be prepared by combining a 5-alkoxy-2-chlorosulfonyl-N-aryl[1,2,4]triazolo[1,5-c]-pyrimidine compound of Formula II:

wherein R represents ($C_1$–$C_3$)alkyl optionally monosubstituted with fluoro, chloro or methoxy or represents 2,2,2-trifluoroethyl and X and Y together represent a biradical fragment of the formula —O—CH═CH—, —CH═CH—O—, —S—CH═CH—, —CH═CH—S—, —($CH_3$)N—CH═CH—, —CH═CH—N($CH_3$)—, —O—$CH_2$—$CH_2$—, —$CH_2$—$CH_2$—O—, —S—$CH_2$—$CH_2$—, —$CH_2$—$CH_2$—S—, —($CH_3$)N—$CH_2$—$CH_2$—, —$CH_2$—$CH_2$—N($CH_3$)—, —($CH_2$)$_3$—, —CH═CH—CH═CH— or —N═CH—CH═CH—, which fragment may be substituted with $CH_3$, with an appropriately substituted aromatic amine compound selected from the following formulas:

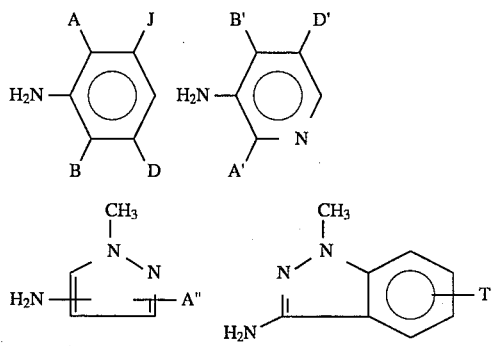

in the presence of pyridine or a methylpyridine compound, and, optionally but preferably, a catalytic amount of dimethyl sulfoxide. The substituents A, B, D, J, A', B', D', A", and T of the aromatic amine compounds are as defined hereinabove.

The preparation is usually accomplished by placing a 5-alkoxy-2-chlorosulfonyl-N-aryl[1,2,4]triazolo[ 1,5-c]pyrimidine compound of Formula II, an aromatic amine, and an inert solvent, such as acetonitrile, N,N-dimethylformamide, N-methyl-2-pyrrolidinone, tetrahydrofuran, and the like, in a vessel and then adding the pyridine or methylpyridine, preferably pyridine, and a catalytic amount of dimethyl sulfoxide. The mixture is allowed to react, typically at ambient temperature, but heating if necessary. After a substantial quantity of the compound of Formula I has formed or a substantial quantity of the chlorosulfonyl compound of Formula II has been consumed, the desired product is recovered, typically by removing the solvent by evaporation, adding water, and removing the liquids from the solid that forms by filtration or centrifugation. The recovered product can be purified, if desired, by extracting with an immiscible organic solvent, such as methylene chloride, and with water. Alternatively, the desired compounds of Formula I can be purified by recrystallization and by other commonly used methods.

Approximately equimolar quantities of the compound of Formula II and the aromatic amine are generally used in the preparation of compounds of Formula I, although a substantial excess of one or the other may be employed. Small to large excesses of the aromatic amine compound are sometimes helpful. The pyridine compound is generally employed in an amount of from at least 1 to about 5 moles per mole of compound of Formula II. Dimethyl sulfoxide is typically used in less than an equimolar amount; amounts over about 0.3 mole per mole of compound of Formula II are usually deleterious. Acetonitrile is often the preferred solvent.

It is sometimes advantageous to prepare the compounds of Formula I by condensing a compound of Formula II with an N-trialkylsilyl derivative of the aromatic amine compound. The method employed is analogous to that described in U.S. Pat. No. 4,910,306 for N-trialkylsilylanilines. The reaction conditions required are essentially the same as those described hereinabove for the condensation of a compound of Formula II with an aromatic amine with the exception that the pyridine compound base may be omitted. An aqueous work-up is typically employed. The substituted N-trialkylsilyl derivatives of the aromatic amine compounds employed can be prepared from the corresponding aromatic amine compounds by treatment with a trialkylsilyl halide and a trialkylamine as described in U.S. Pat. No. 4,910,306 for aniline compounds. Sodium iodide is typically employed as a catalyst when the halide is chloride. The N-trialkylsilylamine compounds are typically prepared and used immediately and without purification.

Compounds of Formula I wherein V represents hydrogen and can also be prepared from the corresponding compounds related to those of Formula I wherein the OR group is replaced by Cl by treatment of said compounds with an appropriate alkali metal alkoxide, such as sodium methoxide or sodium ethoxide. The reaction conditions employed are similar to those used for the related exchange reactions of 2- and 4-chloropyrimidines. Non-aqueous media, such as the corresponding alcohol, are preferred. The starting materials are prepared by methods analogous to those described herein for the preparation of compounds of Formula I.

Compounds of Formula I wherein V represents COR', $CO_2R''$, or $CONR'''2$ (R' represents ($C_1$–$C_4$) alkyl optionally singly to completely substituted with fluorine, R'' represents ($C_1$–$C_4$) alkyl, ($C_3$–$C_4$)alkenyl, or ($C_3$–$C_4$)alkynyl, and R''' represents H or ($C_1$–$C_4$)alkyl) can be prepared from compounds of Formula I wherein V represents hydrogen by acylation with a compound of the formula ClCOR', $ClCO_2R''$, or $ClCONR'''2$, respectively, using conventional procedures known in the art for the acylation of sulfonamides.

The 5-alkoxy-2-chlorosulfonyl[1,2,4]triazolo[1,5-c]pyrimidine compounds of Formula II can be prepared by chloroxidation of the corresponding 5-alkoxy-2-benzylthio[1,2,4]triazolo[1,5-c]pyrimidine compounds of Formula III:

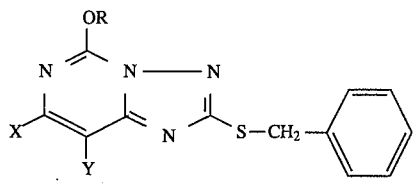

wherein R, X, and Y are defined as before. Similarly, corresponding compounds wherein OR is replaced by Cl can be prepared by chloroxidation of the appropriate chloro compound. The chloroxidation reaction can be carried out under the reaction conditions usually employed for such reactions. In a typical operation, the compound of Formula III is dissolved or suspended in a water-immiscible organic solvent, such as chloroform or dichloromethane, water is added, and then chlorine is added with good agitation to the mixture at temperatures below about 20° C. When the reaction is complete, the organic solvent phase is separated and washed with water. The solvent is typically removed by evaporation to obtain a crude product. This crude product can be purified by standard methods, such as by recrystallization, extraction, or chromatography.

The 5-alkoxy-2-benzylthio[1,2,4]triazolo[1,5-c]-pyrimidine compounds of Formula III can be prepared from hydrazinopyrimidine compounds of Formula IV:

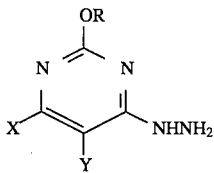

wherein R, X, and Y are defined as before. The process involves cyclization, rearrangement, and alkylation reactions. It can be carried out under reaction conditions usually employed for such transformations. In a typical operation, the hydrazinopyrimidine compound is dissolved or suspended in an organic solvent, such as dioxane, and about one mole each of carbon disulfide and triethylamine is added. The mixture is heated to reflux with stirring, usually under nitrogen because of the flammability of carbon disulfide, for a few hours and then benzyl chloride is added. When the reaction is complete, the desired product is recovered, typically by removing the volatile components by evaporation and recrystallizing the residue. Other standard methods of recovery and purification can be employed. 2-Methylthio analogs of the compounds of Formula III can be prepared analogously.

Compounds of Formula III can also be prepared by reaction of a corresponding compound related to those of Formula III wherein the OR group is replaced by $SCH_3$ or Cl by treatment with the appropriate alkali metal alkoxide in the corresponding alcohol. The reaction takes place under mild conditions.

Compounds of Formula III are often most conveniently prepared by combining a 2-methylthio-4-hydrazinopyrimidine compound of Formula V:

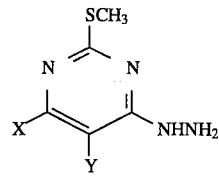

with carbon disulfide and triethylamine, heating the mixture for a short time, and then adding benzyl chloride to obtain a 2-benzylthio-5-methylthio[1,2,4]triazolo[4,3-c]pyrimidine compound as an intermediate. The intermediate is then converted to the desired compound of Formula III by means of its reaction with an appropriate alkali metal alkoxide, such as sodium methoxide, and methyl acrylate, typically in the corresponding alcohol as a solvent. The alkoxide ion causes $RO^-$, the intermediated to rearrange and replaces the 2-methylthio moiety, which moiety is captured by the acrylate ester and is removed from the system. The compounds of Formula III obtained can be recovered by conventional techniques.

The hydrazinopyrimidine compounds of Formulas IV and V can be prepared from the corresponding 2-alkoxy- 4-chloropyrimidine, 2-methylthio-4-chloropyrimidine, or 2,4-dialkoxypyrimidine compounds by standard techniques. Typically, hydrazine and triethylamine are added to the appropriate pyrimidine compound dissolved in a solvent and the reaction mixture is allowed to react. The desired compounds of Formulas IV and V can be recovered by standard methods.

The 2-alkoxy-4-chloropyrimidine, 2,4-dialkoxypyrimidine, 2,4-dichloropyrimidine, and 2-methylthio-4-alkoxypyrimidine compounds utilized as starting materials in the preparative methods described above can be prepared in a variety of ways depending on the identity of the biradical defined by X and Y. Several specific examples are given in the experimental part. These methods can readily be adapted by those of ordinary skill in the art to obtain each of the starting materials required to prepare the compounds of Formulas IV and V.

Some of the substituted aniline, 3-aminopyridine, 3-, 4-, and 5-aminopyrazole, and 3-aminoindazole compounds that are required as intermediates for the compounds of Formula I are known in the art or can be prepared by the general methods known in the art. Other such compounds can be prepared by the methods of the Examples and by conventional modifications thereof readily apparent to those of ordinary skill in the art.

While it is possible to utilize the ring annulated 5-alkoxy-N-aryl[1,2,4]triazolo[1,5-c]pyrimidine- 2-sulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanol-ammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as waters before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence and postemergence herbicides. They can be employed at non-selective (higher) rates of application to control essentially all of the vegetation in an area and, in some cases, at selective (lower) rates of application for the selective control of undesirable vegetation in grass crops, such as corn, wheat, barley, and rice as well as in broadleaf crops, such as soybeans and cotton. While each of the compounds encompassed by Formula I is within the scope of the invention, the degree of herbicidal activity, the selectivity, and the spectrum of weed control obtained varies depending upon the substituents present.

The term herbicide is used herein to mean an active ingredient which controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote selective herbicidal action. Generally, it is preferred to apply the compounds of Formula I postemergence to relatively immature plants to achieve the maximum control of broadleaf weeds.

Application rates of about 0.001 to about 1 Kg/Ha are generally employed in postemergence operations; for preemergence applications, rates of about 0.01 to about 10 Kg/Ha are generally employed. The higher rates designated generally give non-selective control of a broad variety of undesirable vegetation. The lower rates typically give selective control and, by judicious election, many can be employed in the locus of crops.

EXAMPLES

The following Examples are presented to illustrate the various aspects of this invention and should not be construed as limitations to the claims.

1. Preparation of 2-Methylthio-4(3H)-oxocyclopenteno[d]pyrimidine.

A solution of S-methylisothiourea in ethanol was prepared by mixing 9.8 g (gram) (35 mmol (millimole)) of S-methylisothiourea sulfate in 100 mL (milliliters) of ethanol with 3.9 g (70 mmol) of potassium hydroxide in 25 mL of ethanol at 0° C. and to this cold solution was added with stirring 4.74 mL (32 mmol) of ethyl cyclopentanone-2-carboxylate. The resultant mixture was allowed to warm to ambient temperature and was stirred overnight. A small amount of white solid formed. The mixture was concentrated to about 50 mL by evaporation under reduced pressure resulting in the formation of a white precipitate. The mixture was heated at reflux for 3 hours at which time there did not appear to be any further reaction taking place as determined by high pressure liquid chromatography (HPLC). The mixture was acidified by adding acetic acid and the volatile components were removed by evaporation under reduced pressure. Water (100 mL) was added and after 1 hour, the solids present were collected by filtration and dried to obtain 1.75 g (30 percent of theory) of the title compound as a tan solid melting at 251°–255° C. The proton nuclear magnetic resonance spectrum (NMR) was compatible with the assigned structure.

Elemental Analysis $C_8H_{10}N_2OS$

Calc.: % C, 52.7; % H, 5.53; % N, 15.4; % S, 17.6

Found: % C, 53.0; % H, 5.66; % N, 15.6; % S, 17.5

2. Preparation of 4-Chloro-2-methylthiocyclopenteno[d]pyrimidine

A solution of 44.5 g (244 mmol) of 2-methylthio- 4(3H)-oxocyclopenteno[d]pyrimidine in 150 mL of dry acetonitrile was prepared and to this was added 46 mL of phosphorus oxychloride and 31 mL of N,N-dimethylaniline. The mixture was heated to reflux with stirring for 2 hours and was then concentrated by evaporation under reduced pressure. The residue was poured slowly into 400 mL of cold water with ice-bath cooling and stirring. The resulting mixture was diluted with 1 L (liter) of methylene chloride and the emulsion that formed was allowed to stand overnight. The mixture was filtered and the organic layer was separated, dried over magnesium sulfate, and concentrated by evaporation under reduced pressure to obtain a black solid. This was diluted with 2 L of diethyl ether and, after standing over a weekend, the mixture was filtered by gravity and the ether was evaporated from the filtrate to obtain a tan solid. This solid was extracted with three 1 L portions of hexane and the combined extracts were concentrated by evaporation under reduced pressure to obtain the title compound as a yellow crystalline solid that appeared to be about 95 percent pure by HPLC.

Elemental Analysis $C_8H_9ClN_2S$

Calc.: % C, 47.9; % H, 4.50; % N, 14.0; % S, 16.0

Found: % C, 50.0; % H, 4.50; % N, 14.2; % S, 15.8

3. Preparation of 4-Hydrazino-2-methylthiocyclopenteno-[d]pyrimidine

Hydrazine monohydrate (12 mL (250 mmol)) was added to a solution of 23.6 g (118 mmol) of 4-chloro-2-methylthiocyclopenteno[d]pyrimidine in 590 mL of ethanol with stirring at ambient temperature. Little reaction appeared to take place a over 2 days so the mixture was heated to reflux for 4 hours at which time the reaction appeared to be complete as determined by HPLC. The ethanol was removed by evaporation under reduced pressure and the residue was diluted with 300 mL of water and 500 mL of methylene chloride The resulting mixture was allowed to stir overnight. The phases were separated and the organic phase was dried over magnesium sulfate and concentrated by evaporation under reduced pressure. The residue was slurried with hexane and the insoluble solids were recovered by filtration and air dried to obtain 17.4 g (75 percent of theory) of the title compound as a white solid melting at 149°–151° C. The proton NMR spectrum was compatible with the assigned structure.

Elemental Analysis $C_8H_{12}N_4S$

Calc.: % C, 49.0; % H, 6.16; % N, 28.6; % S, 16.3

Found: % C, 49.2; % H, 6.47; % N, 28.7; % S, 16.4

4. Preparation of 2-Benzylthio-5-methylthiocyclopenteno-[d][1,2,4]triazolo[4,3-c]pyrimidine A mixture of 16.66 g (98.4 mmol) of 4-hydrazino- 2-methylthiocyclopenteno[d]pyrimidine in 200 mL of dioxane was prepared and 12 mL (200 mmol) of carbon disulfide and 17.7 mL (200 mmol) of triethylamine were added to this with stirring at ambient temperature. The solids dissolved in about 15 min and then the mixture was heated to reflux for 1 hour. The heat was removed and 12.4 mL (110 mmol) of benzyl chloride was added with stirring. The mixture was allowed to react at ambient temperature for 1 hour and was then heated at reflux for 1.5 hour. The volatile components of the resulting mixture were removed by evaporation under reduced pressure and the residue was dissolved in 300 mL of methylene chloride. The resulting solution was washed three times with 100 mL portions of water, dried over magnesium sulfate, and concentrated by evaporation under reduced pressure to obtain a brown oil. The oil was triturated with hexane and the tan solid that formed was recovered by filtration and dried under reduced pressure overnight to obtain 24.9 g (77 percent of theory) of the title compound melting at 150°–153° C. The proton NMR spectrum was compatible with the assigned structure.

Elemental Analysis $C_{16}H_{16}N_4S_2$

Calc.: % C, 58.5; % H, 4.91; % N, 17.1; S, % 19.5

Found: % C, 58.4; % H, 5.12; % N, 17.4; S, % 19.3

5. Preparation of 2-Benzylthio-5-methoxycyclopenteno [d]-[ 1,2,4] triazolo[1,5-c]pyrimidine.

3-Benzylthio-5-methylthiocyclopenteno[d] [ 1,2,4]triazolo[4,3-c]pyrimidine (915.5 g, 47.2 mmol) was mixed with 100 mL of methanol and 6.4 mL (70 mmol) of methyl acrylate and then 2.7 mL (12 mmol) of 25 percent sodium methoxide in methanol solution was added at ambient temperature with stirring. The solids that were initially present mostly dissolved after about 1 hour and then a new white solid began to form. The reaction appeared to be complete by HPLC after a total of about 2.7 hours. The mixture was then acidified with acetic acid and the insoluble solids were collected by filtration. The filtrate was concentrated by evaporation under reduced pressure to obtain more solids. The solids were combined and dissolved in methylene chloride. The resulting solution was washed with three 200 mL portions of water, dried over magnesium sulfate, and concentrated under reduced pressure to obtain a brown oil. This oil was triturated with hexane and the tan solid that formed was recovered by filtration and dried to obtain 12.9 g (87 percent of theory) of the title compound melting at 93°–95° C. The proton NMR spectrum was compatible with the assigned structure.

Elemental Analysis $C_{16}H_{16}N_4S$

Calc.: % C, 61.5; % H, 5.16; % N, 17.9; % S, 10.3

Found: % C, 61.4; % H, 5.28; % N, 17.9; % S, 10.2

6. Preparation of 2-Chlorosulfonyl-5-methoxycyclopenteno-[ d][ 1,2,4] triazolo[1,5c]pyrimidine.

2-Benzylthio-5-methoxycyclopenteno[ d][ 1,2,4] -triazolo[ 1,5-c]pyrimidine (2.12 g, 6.8 mmol) was dissolved in 10 mL of methylene chloride and 7 mL of 3N hydrochloric acid was added. This mixture was cooled to 3° C. and 30 mL of 5.25 percent by weight aqueous sodium hypochlorite (21 mmol) was added with stirring and cooling. The mixture was allowed to react for about 1.5 hours and the layers were then separated. The organic layer was dried and concentrated by evaporation under reduced pressure to obtain a tan oil. Pentane was added and the mixture was allowed to stand overnight during which time the oil solidified. The resulting tan solid was collected by filtration and dried under reduced pressure at 50° C. to obtain 1.72 g (88 percent of theory) of the title compound. The proton NMR spectrum was compatible with the assigned structure.

7. Preparation of N-(2,6-Dichlorophenyl)-5-methoxycyclopenteno[ d][1,2,4]triazolo[1,5-c]pyrimidine-2-sulfonamide.

A solution was prepared by combining 30 mL of a 0.60M in acetonitrile (18 mmol) solution of 2,6-dichloro-N-trimethylsilylaniline and 1.71 g (5.9mmol) of 2-chloro-sulfonyl-5-methoxycyclopenteno[d][1,2,4]triazolo[1,5-c]pyrimidine and to this was added at ambient temperature under nitrogen with stirring 0.09 mL of dimethyl sulfoxide. The mixture was allowed to react overnight and the volatiles were then removed by evaporation under reduced pressure. The residue was flash chromatographed on 240 mesh silica gel eluting with mixtures of methylene chloride and ethanol (500 mL of 100/0 and 1 L of 98/2) to obtain a tan solid. This solid was extracted with hexane and dried under reduced pressure to obtain 0.61 g (25 percent of theory) of the title compound as a tan solid melting at 211°–213° C. The proton NMR spectrum was compatible with the assigned structure.

Elemental Analysis $C_{15}H_{13}Cl_2N_5O_3S$

Calc.: % C, 43.5; % H, 3.16; % N, 16.9; % S, 7.74

Found: % C, 43.8; % H, 3.21; % N, 16.5; % S, 7.69

8. Preparation of N-Ethoxysarbonyl-N'-(2-methoxycarbonyl-3-pyridinyl)thiourea.

A mixture of 22.3 g (0.147 mol) of 2-amino-3-methoxycarbonylpyridine and 19.2 g (0.147 mol) of ethoxycarbonyl isothiocyanate in 100 mL of chloroform was heated to reflux with stirring. A solid began to precipitate almost immediately. Another 100 mL of chloroform and another 3 g of the ethoxycarbonyl isothiocyanate were added, the latter in 1-g portions. The mixture was stirred at reflux for a short period, at ambient temperature overnight, and at reflux for another hour. The volatile components were removed by evaporation under reduced pressure and the solid residue was diluted with ether, recovered by filtration, and dried. The resulting product was 38.3 g of the title compound as a yellow powder melting at 198°–199° C. with decomposition.

Elemental Analysis $C_{11}H_{13}N_3O_4S$

Calc.: % C, 46.6; % H, 4.63; % N, 14.8; % S, 11.3

Found: % C, 46.8; % H, 4.73; % N, 15.0; % S, 11.0

9. Preparation of 4-Hydroxypyrido[3,2-d]pyrimidine-2-thiol

A mixture of 37.2 g (0.13 mol) of N-ethoxycarbonyl-N'-( 2-methoxycarbonyl-3-pyridinyl)thiourea and 33 mL of 25 percent sodium methoxide in methanol (0.14 mol) in 500 mL of absolute ethanol was heated to reflux with stirring. A solid began to form after about 5 min and after 1 hour heating was discontinued and the volatile components were removed by evaporation under reduced pressure. The residue was diluted with water, acidified with acetic acid, and filtered to recover the solids. The solids were extracted on the filter with ether and then with acetone to obtain a fine powder that was difficult to filter. This was extracted with ether again (added while some acetone was still present) and, finally, with hexane to obtain the 23.3 g of title compound as a more easily filtered pale yellow granular solid melting above 300° C.

10. Preparation of 4-Hydroxy-2-methylthiopyrido[3,2-d]pyrimidine

A mixture of 22.1 g (0.123 mot) of 4-hydroxypyrido[ 3,2-d]pyrimidine-2-thiol, 65 mL of 25 percent sodium methoxide in methanol (0.28 mol), 8.9 mL (20.1 g, 0.142 mol) of methyl iodide, and 500 mL of methanol was prepared and allowed to react at ambient temperature with stirring until the starting material thiol disappeared as determined by high pressure liquid chromatography (HPLC). The mixture was then acidified with acetic acid and the volatile components were removed by evaporation under reduced pressure. The residue was diluted with water and the solids were recovered by filtration, washed with ether, and dried overnight in a vacuum oven. The resultant white powder was the title compound melting at 229°–231° C.

Elemental Analysis $C_8H_7N_3OS$

Calc.: % C, 49.7; % H, 3.66; % N, 21.8; % S, 16.6

Found: % C, 49.6; % H, 3.76; % N, 21.7; % S, 16.3

11. Preparation of 4-Chloro-2-methylthiopyrido[3,2-d]pyrimidine

A mixture of 19.0 g (98 mmol) of 4-hydroxy-2-methylthiopyrido[ 3,2-d]pyrimidine, 36.5 mL (60 g, 390 mmol) of phosphorus oxychloride and 200 mL of acetonitrile was prepared and heated to reflux with stirring. Since not much appeared to happen, about 1 mL of N,N-dimethylformamide was added. The solids then all went into solution in about 10 min. After about 2 hours, the volatiles were removed by evaporation under reduced pressure and the residue was diluted with dichloromethane. The resulting mixture was carefully washed with water, dried over magnesium sulfate, and concentrated by evaporation under reduced pressure. The residue was diluted with hexane and the solids were recovered by filtration and dried to obtain 17.8 g of the title compound melting at 120°–121° C.

Elemental Analysis $C_8H_6ClN_3S$

Calc.: % C, 45.4; % H, 2.86; % N, 19.9; % S, 15.2

Found: % C, 45.5; % H, 2.94; % N, 20.1; % S, 15.1

12. Preparation of 4-Hydrazino-2-methylthiopyrido[3,2-d]pyrimidine

Hydrazine hydrate (13.0 mL (13.3 g, 237 mmol)) was added at ambient temperature with stirring to a mixture of 16.7 g (79 mmol) of 4-chloro-2-methylthiopyrido[ 3,2-d]pyrimidine in 200 mL of ethanol. There was a slight exotherm and the mixture thickened and then became more mobile again. After 30 min, the volatile components were removed by evaporation under reduced pressure. The residue was diluted with water and the solids were recovered by filtration, washed with ether, and dried to obtain 15.7 g of the title compound as a brown powder melting above 300° C.

Elemental Analysis $C_8H_9N_5S$

Calc.: % C, 46.4; % H, 4.38; % N, 33.8; % S, 15.5

Found: % C, 46.4; % H, 4.61; % N, 33.6; % S, 15.2

13. Preparation of 3-Benzylthio-5-methylthiopyrido-[3,2-e][1,2,4]triazolo[4,3-c]pyrimidine 4-Hydrazino-2-methylthiopyrido[3,2-d]pyrimidine (14.5 g, 70 mmol) was combined with 200 mL of dioxane, 12.6 mL (16.0 g, 210 mmol) of carbon disulfide, and 29 mL (21.2 g, 210 mmol) of triethylamine and the mixture was heated at reflux with stirring for 4 hours during which time another 50 mL of dioxane was added to facilitate stirring. The mixture was allowed to cool, 13.3 g (105 mmol) of benzyl chloride was added, and the resulting mixture was allowed to stir overnight. Another 6 g of benzyl chloride and 25 mL of triethylamine were added and the mixture was heated to reflux with stirring for a short period. The volatile components were removed by evaporation under reduced pressure and the residue was diluted with dichloromethane and water. The resultant emulsion was filtered to obtain separable phases and the organic phase was washed with water, dried over magnesium sulfate, and concentrated by evaporation under reduced pressure. The residue was diluted with hexane and the resulting black solid was recovered by filtration. This solid was diluted with dichloromethane and the solution obtained was filtered through silica gel. Evaporation of the filtrate under reduced pressure gave a black solid that was diluted with ether and recovered by filtration to obtain 18.8 g the title compound melting at 157°–158° C. The proton NMR spectrum was compatible with the assigned structure. Work up of the filtrate gave an additional 6 g of impure title compound as a black oil.

Elemental Analysis $C_{16}H_{13}N_5S_2$

Calc.: % C, 56.6; % H, 3.86; % N, 20.0; % S, 18.9

Found: % C, 56.9; % H, 3.80; % N, 20.3; % S, 19.0

14. Preparation of 2-Benzylthio-5-methoxypyrido[3,2-e][1,2,4]triazolo[1,5-c]pyrimidine A mixture of 17.7 g (52 mmol) of 3-benzylthio-5-methylthiopyrido[3,2-e][1,2,4]triazolo[4,3-c]pyrimidine in 200 mL of methanol was prepared and to this was added at ambient temperature with stirring 8.5 mL (7.8 g, 78 mmol) of ethyl acrylate and 2.4 mL of 25 percent sodium methoxide in methanol (10 mmol). Everything dissolved fairly quickly and after 15 min new precipitate formed. After about 1 hour the mixture was acidified with acetic acid and the volatile components were removed by evaporation under reduced pressure. The residue was dissolved in dichloromethane and the resulting solution was washed with water, dried over magnesium sulfate, and concentrated by evaporation under reduced pressure. The residue was diluted with ether, recovered by filtration, and dried to obtain 14.6 g of the title compound as a brown powder melting at 282°–284° C. with decomposition.

Elemental Analysis $C_{16}H_{13}N_5OS$

Calc.: % C, 59.4; % H, 4.05; % N, 21.7; % S, 9.92

Found: % C, 59.3; % H, 3.92; % N, 21.3; % S, 10.3

15. Preparation of 2-Chlorosulfonyl-5-methoxypyrido[3,2-e][1,2,4]triazolo[1,5-c]pyrimidine 2-Benzylthio-5-methoxypyrido [3,2-e] [1,2,4] triazolo[1,5-c]pyrimidine (13.5 g, 42 mmol) was placed in a mixture of 100 mL of dichloromethane and 100 mL of water and the combination was cooled to about 5° C. Chlorine gas (15.8 g, 233 mmol) was added slowly to this with stirring and cooling to keep the temperature at about 3°–7° C. When all of the chlorine had been added, the mixture was stirred another 30 min and then the two liquid phases were separated. The organic phase was dried over a mixture of magnesium and sodium sulfates and was then concentrated by evaporation under reduced pressure to obtain an oily residue. The residue was triturated with hexane, recovered by filtration, and dried to obtain 11.0 g of the title compound as a yellow powder melting at 172°–174° C. with decomposition. The proton NMR spectrum of this was compatible with the assigned structure.

16. Preparation of N-(2,6-dichlorophenyl)-5-methoxypyrido[3,2-e][1,2,4]triazolo[1,5-c]pyrimidine-2-sulfonamide A mixture of 2.0 g (6.7 mmol) of 2-chlorosulfonyl-5-methoxypyrido[3,2-e][1,2,4]triazolo[1,5-c]pyrimidine, 2.2 g (13.3 mmol) of 2,6-dichloroaniline, 0.50 g (67 mmol) of pyridine, and 30 mL of dry acetonitrile was prepared and to this was added with stirring at ambient temperature 95 microliters (1.3mmol) of dimethyl sulfoxide. The mixture was allowed to react overnight and was then concentrated by evaporation under reduced pressure. The residue was diluted with dichloromethane and water and the resulting mixture was filtered to remove the insoluble solids. The organic phase was recovered and the dichloromethane was removed by evaporation under reduced pressure. The residue was diluted with hexane, recovered by filtration, and redissolved in dichloromethane. The resulting solution was filtered through silica gel and concentrated by evaporation under reduced pressure. The residue was diluted with hexane, recovered by filtration, and dried to obtain 0.25 g of the title compound as a light tan powder melting at 290°–293° C. with decomposition. The proton NMR spectrum of this was compatible with the assigned structure.

Elemental Analysis $C_{15}H_{10}Cl_2N_6O_3S$

Calc.: % C, 42.4; % H, 2.37; % N, 19.8; % S, 7.54

Found: % C, 42.6; % H, 2.58; % N, 18.7; % S, 7.23

17. Preparation of N-Ethoxycarbonyl-N'-(2-methoxycarbonyl-3-thienyl)thiourea Methyl 3-amino-2-thiophenecarboxylate (5.0 g (32 mmol) was dissolved in 16 mL of chloroform and to this solution 4.17 g (32 mmol) of ethoxycarbonyl isothiocyanate was added slowly with stirring at ambient temperature. A precipitate began to appear after a few minutes and after 20 min the volatile components were removed by evaporation under reduced pressure. The tan solid residue obtained was diluted with 20 mL of ether and allowed to stir for about 20 min and then 100 mL of hexane was added. The insoluble solids were recovered by filtration and dried to obtain 8.51 g of the title compound as a tan solid melting at 165°–167° C.

Elemental Analysis $C_{10}H_{12}N_2O_4S_2$

Calc.: % C, 41.7; % H, 4.19; % N, 9.72; % S, 22.2

Found: % C, 41.3; % H, 4.41; % N, 9.59; % S, 22.3

18. Preparation of 4-Hydroxyphiopheno[3,2-d]pyrimidine-2-thiol

A solution of 23.9 g (83 mmol) of N-ethoxy-carbonyl-N'-(2-methoxycarbonyl-3-thienyl)thiourea in 250 mL of methanol was prepared and to this was added 22 mL of 25 percent sodium methoxide in methanol (99 mmol). The mixture was heated to reflux with stirring. A tan solid began to precipitate after about 1 hour and after 2 hours the mixture was allowed to cool and the solid was recovered by filtration. The filtrate was concentrated by evaporation under reduced pressure to obtain additional solid. The solids were combined, diluted with 500 mL of water (the mixture stirred for 2 hours), recovered by filtration, and dried. The 15.1 g of tan solid title compound obtained melted over 250° C. and had a proton NMR spectrum that was consistent with the assigned structure.

Elemental Analysis $C_6H_4N_2OS_2$

Calc.: % C, 39.1; % H, 2.19; % N, 15.2; % S, 34.8

Found: % C, 39.4; % H, 2.29; % N, 15.0; % S, 34.9

19. Preparation of 4-Hydroxy-2-methylthiohiopheno[3,2-d] pyrimidine

4-Hydroxythiopheno[3,2-d] pyrimidine-2-thiol (14.6 g (79 mmol)) was mixed with 80 mL of methanol and 36 mL of 25 percent sodium methoxide in methanol (158 mmol) and then 5.4 mL (2.28 g, 87 mmol) of methyl iodide was added. The mixture was heated to reflux with stirring for 2 hours. It was then allowed to cool and was acidified with 10 mL of acetic acid. The solids present were recovered by filtration and the filtrate was concentrated by evaporation under reduced pressure to obtain more solids. The solids were combined, diluted with 500 mL of water, recovered by filtration, and dried to obtain 15.6 g of the title compound as a tan solid melting over 250° C. The proton NMR spectrum was consistent with the assigned structure.

Elemental Analysis $C_7H_6N_2OS_2$

Calc.: % C, 42.4; % H, 3.05; % N, 14.1; % S, 32.3

Found: % C, 42.0; % H, 3.39; % N, 13.8; % S, 32.5

20. Preparation of 4-Chloro-2-methylthiopheno [3,2-d] pyrimidine

4-Hydroxy-2-methylthiothiopheno[3,2-d] pyrimidine (15.4 g, 78 mmol) was combined with 50 mL of dry acetonitrile and 29 mL (312 mmol) of phosphoryl chloride and 10 mL (78 mmol) of N,N-dimethylaniline were added with stirring. The mixture was heated to reflux with stirring for 2 hours. It was then allowed to cool and most of the acetonitrile was removed by evaporation under reduced pressure. The residue was poured slowly into 200 mL of cold water with cooling and agitation. The resulting mixture was extracted with 4×500 mL of ether and the combined ethereal extracts were dried over magnesium sulfate and concentrated by evaporation under reduced pressure. The 15.3 g of tan solid title compound obtained melted at 115°–118° C. and had a proton NMR spectrum consistent with the assigned structure.

Elemental Analysis $C_7H_5ClN_2S_2$

Calc.: % C, 38.8; % H, 2.33; % N, 12.9; % S, 29.6

Found: % C, 38.7; % H, 2.34; % N, 13.0; % S, 29.5

21. Preparation of 4-Hydrazino-2-methylthiopheno[3,2-d]pyrimidine

4-Chloro-2-methylthiothiopheno[3,2-d]pyrimidine (15.26 g, 70.4 mmol) was mixed with 400 mL of ethanol and then 7.2 mL (148 mmol) of hydrazine hydrate was added with stirring at ambient temperature and the mixture was allowed to stir overnight. The solid materials present were recovered by filtration and the filtrate was evaporated to dryness under reduced pressure to obtain additional solid material. All of the solids were combined and mixed vigorously with a mixture of 500 mL of dichloromethane and 500 mL of water for 6 hours. The solids present were recovered by filtration and dried to obtain 13.9 g of the title compound as a slightly yellow solid melting at 242°–244° C. The proton NMR spectrum was consistent with the assigned structure.

Elemental Analysis $C_7H_8N_4S_2$

Calc.: % C, 39.6; % H, 3.80; % N, 26.4; % S, 30.1

Found: % C, 39.4; % H, 3.84; % N, 26.2; % S, 30.5

22. Preparation of 3-Benzylthio-5-methylthiothieno[3,2-e][1,2,4]triazolo[4,3-c]pyrimidine 4-Hydrazino-2-methylthiothiopheno[3,2-d]pyrimidine (13.4 g (63 mmol) was combined with 200 mL of 1,4-dioxane, 7.6 mL (126 mmol) of carbon disulfide, and 17.6 mL (126 mmol) of triethylamine at ambient temperature with stirring. After 1 hour another 7.6 mL of carbon disulfide was added and, after 20 min, the mixture was heated to reflux for 1 hour. An 8.7 mL portion of benzyl chloride was added to the hot solution and the mixture was stirred for 2 hours. The solids present were recovered by filtration and the filtrate was concentrated by evaporation under reduced pressure to obtain additional solids. The combined solids were diluted with 500 mL of dichloromethane and 500 mL of water and stirred for 1 hour and then another 1 L of dichloromethane was added. The solids present were recovered by filtration and dried to obtain 10.5 g of the title compound melting at 209°–211° C. The filtrate was dried over magnesium sulfate and concentrated by evaporation under reduced pressure to obtain 9.20 g of additional title compound as a yellow solid. The proton NMR spectra of both product fractions were consistent with the assigned structure.

Elemental Analysis $C_{15}H_{12}N_4S_3$

Calc.: % C, 52.3; % H, 3.51; % N, 16.3; % S, 27.9

Found: % C, 52.1; % H, 3.60; % N, 16.2; % S, 27.9

23. Preparation of 2-Benzylthio-5-methoxythieno[3,2-e][1,2,4]triazolo[1,5-c]pyrimidine 3-Benzylthio-5-methylthiothieno[3,2-e][1,2,4]-triazolo[4,3-c]pyrimidine (19.2 g (57.2 mmol)was mixed with 100 mL of methanol and to this was added with stirring 7.7 mL (86 mmol) of methyl acrylate and 3.3 mL of 25 percent sodium methoxide in methanol. After 2 hours at ambient temperature, the mixture was heated to reflux for about 2.5 hours during which time another 10 mL of 25 percent sodium methoxide in methanol was added. The mixture was stirred at ambient temperature overnight and then another 5 mL of the 25 percent sodium methoxide in methanol was added and the mixture heated to reflux again for 2 hours. The resulting mixture was acidified with acetic acid and was then concentrated by evaporation under reduced pressure to obtain a tan solid. This was dissolved in 600 mL of dichloromethane and the solution obtained was washed 3×100 mL with water, dried over magnesium sulfate, and concentrated by evaporation under reduced pressure. The tan, solid residue was flash chromatographed on silica gel (240–400 mesh, 5×20 cm (centimeter) column) eluting with mixtures of hexane and ethyl acetate ranging from 90:10 to 50:50. The second compound to elute was collected to obtain 12.6 g of the title compound as a nearly white solid melting at 160°–162° C. The proton NMR spectra of this was consistent with the assigned structure.

Elemental Analysis $C_{15}H_{12}N_4OS_2$

Calc.: % C, 54.9; % H, 3.68; % N, 17.1; % S, 19.5

Found: % C, 54.3; % H, 3.79; % N, 17.0; % S, 19.6

24. Preparation of 2-Chlorosulfonyl-5-methoxythieno[3,2-e][1,2,4]triazolo[1,5-c]pyrimidine 2-Benzylthio-5-methoxythieno[3,2-e][1,2,4] triazolo[1,5-c]pyrimidine (12.1 g, 37 mmol) was dissolved in a mixture of 150 mL of chloroform and 75 mL of water and the mixture was cooled to about 0° C. Chlorine gas (8.5 g, 120 mmol) was added to this slowly with stirring at about 0° C. After about 30 min, the mixture was allowed to warm to ambient and another 8.0 g (113 mmol) of chlorine was added. The mixture was allowed to react for about 1 hour and then the organic phase was separated and recovered, dried over magnesium sulfate, filtered, and concentrated by evaporation under reduced pressure. The oily residue obtained was crystallized by adding 50 mL of ether and the mixture was diluted with 200 mL of hexane. The solid was recovered by filtration and dried to obtain 10.0 g of the title compound as a slightly yellow solid melting at 166°–167° C. The proton NMR spectra of this was consistent with the assigned structure.

25. Preparation of N-(2,6-Dichlorophenyl)-5-methoxythieno[3,2-e] [1,2,4]triazolo[1,5-c]pyrimidine-2-sulfonamide 2-Chlorosulfonyl-5-methoxythieno[3,2-e] [1,2,4] triazolo[ 1,5-c]pyrimidine (1.5 g, 4.9 mmol) and 2,6-dichloroaniline (1.59 g, 9.8 mmol) were dissolved in 20 mL of acetonitrile and to this was added under nitrogen at ambient temperature with stirring 0.40 mL (4.9 mmol) of pyridine and 0.05 mL of dimethyl sulfoxide. The mixture was allowed to stir overnight and was then concentrated by evaporation under reduced pressure. The residue was flash chromatographed on silica gel and fractions containing the major product were recovered. Evaporation of the solvents under reduced pressure gave a white powder. This was extracted with 200 mL of hexane and the insoluble white solid was dried to obtain 1.0 g of the title compound melting at 224°–226° C. The proton NMR spectra of this was consistent with the assigned structure.

Elemental Analysis $C_{14}H_9Cl_2N_5O_3S_2$

Calc.: % C, 39.1; % H, 2.11; % N, 16.3; % S, 14.9

Found: % C, 39.4; % H, 2.16; % N, 16.2; % S, 15.0

26. Preparation of 3-Amino-2-fluoro-4-methylpyridine

To a solution of 10.1 g (65 mmol) of 2-fluoro- 4-methyl-3-nitropyridine in 200 mL of ethyl acetate was added 25 g (0.40 mol) of acetic acid and 0.8 g of 5 percent palladium on carbon catalyst. This mixture was shaken under 50 psig (pounds per square inch gauge) (2400 kiloPascals) pressure of hydrogen for 18 hours, was filtered, and was concentrated by evaporation under reduced pressure to obtain an oil. This oil was partitioned between dilute aqueous sodium bicarbonate and ether. The organic phase was recovered, dried over magnesium sulfate, and filtered. The filtrate was concentrated by evaporation under reduced pressure and the residue was purified by column chromatography to obtain 7.2 g (88 percent of theory) of the title compound as a colorless solid melting at 63°–64° C. Nuclear Magnetic Resonance Spectrum (200 MHz (megaHertz), $CDCl_3$): $^1H$: 7.4 (d, 1H, J=5.0); 6.8 (d, 1H, J=5.0); 3.7 (br, 2H); 2.1 (s, 3H); $^{13}C$: 152.6 (d, J=229); 134.1 (d, J=8.6); 133.8 (d, J=14.5); 128.1 (d, J=27.1); 123.3, 16.4 (d, J=4.1).

27. Preparation of 3-Amino-2-chloro-4-methoxypyridine

To a solution of 6.4 g (51 mmol) of 3-amino-4-methoxypyridine in 30 mL of 37 percent aqueous hydrochloric acid was slowly added 7.8 g of 30 percent aqueous hydrogen peroxide at room temperature with stirring. After 30 min this solution was slowly poured into 300 mL of saturated aqueous sodium bicarbonate and the resulting mixture was extracted with ether (3×200 mL). The ethereal extracts were combined, dried over magnesium sulfate, and filtered. The filtrate was concentrated by evaporation under reduced pressure to obtain a light brown solid. This solid was purified by column chromatography (17:83 acetone:hexane) to obtain 6.54 g (81 percent of theory) of the title compound as colorless needles melting at 86°–87° C.

Elemental Analysis $C_6H_7ClN_2O$

Calc.: % C, 45.4; % H, 4.45; % N, 17.7

Found: % C, 45.4, % H, 4.65; % N, 17.8

Nuclear Magnetic Resonance Spectrum (200 MHz, $CDCl_3$) $^1H$: 7.7 (d, 1H, J=5.4); 6.6 (d, 1H, J=5.4), 4.0 (br, 2H); 3.8 (s, 3H); $^{13}C$: 153.3, 138.5, 135.6, 129.9, 105.2, 55.9.

28. Preparation of 3-Amino-4-fluoro-1-methylindazole

Methylhydrazine (4.96 g, 108 mmol) was added to a solution of 15.0 g (108 mmol) of 2,6-difluorobenzonitrile in 150 mL of ethanol and the mixture was heated to reflux with stirring for 72 hours. The volatiles were then removed by evaporation under reduced pressure and residue was dissolved in dichloromethane. The resulting solution was washed with water, dried over magnesium sulfate, and evaporated to dryness under reduced pressure to obtain a white solid. This was recrystallized from ethanol to obtain 10.1 g (57 percent of theory) of the title compound as white crystals melting at 125°–127° C.

Elemental Analysis $C_8H_8N_3F$

Calc.: % C, 58.2; % H, 4.88; % N, 25.4

Found: % C, 58.7, % H, 4.76; % N, 25.9

Nuclear Magnetic Resonance Spectrum (200 MHz, $CDCl_3$) $^1H$: 7.19 (m, 1H); 7.11 (d, 1H, J=8.4), 6.59 (d of d, 1H, J=8.4, 3.3), 5.26 (brs, 2H), 3.72 (s, 3H); $^{13}C$: 157.35, 154.88, 146.20, 146.18, 143.85, 143.76, 127.62, 127.55, 105.31, 105.27, 103.44, 103.24, 101.96, 101.78, 34.74.

29. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kiloPascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 2.

TABLE 2

POSTEMERGENCE HERBICIDAL ACTIVITY

| Cpd. No. | Rate, ppm | Cockle-bur | Jimson-weed | Lambs-quarters | Morning-glory | Velvet-leaf | Veron-ica | Wild Buck-wheat | Black-grass | Johnson-grass |
|---|---|---|---|---|---|---|---|---|---|---|
| 1 | 2000 | 85 | 95 | 80 | 95 | 100 | 100 | 85 | 20 | 40 |
| 2 | 250 | 40 | 80 | 0 | 80 | 100 | 100 | 30 | 0 | 0 |
| 3 | 500 | 35 | 85 | 85 | 75 | 25 | — | 65 | 80 | 85 |
| 4 | 125 | 85 | 65 | 0 | 90 | 80 | 90 | 75 | 88 | 85 |
| 5 | 500 | 90 | — | 88 | 86 | 85 | 50 | 50 | 90 | 50 |
| 6 | 15.6 | 100 | 80 | 0 | 50 | 80 | 100 | 80 | 25 | 0 |
| 7 | 7.8 | 90 | 100 | 0 | 90 | 85 | 35 | 85 | 10 | 0 |
| 8 | 250 | 90 | 70 | 70 | 80 | 70 | 80 | 75 | 70 | 65 |
| 9 | 125 | 90 | 80 | 85 | 90 | 70 | 80 | 40 | 70 | 90 |
| 10 | 1000 | 100 | 50 | 40 | 40 | 90 | 100 | 40 | 60 | 70 |
| 11 | 2000 | 75 | 80 | 40 | 30 | 80 | 60 | 30 | 40 | 0 |
| 12 | 15.6 | 100 | 80 | 50 | 60 | 85 | 75 | 60 | 90 | 75 |
| 13 | 31.3 | 85 | 90 | 30 | 65 | 100 | 100 | 100 | 80 | 80 |
| 14 | 15.6 | 100 | 70 | 30 | 85 | 88 | 85 | 60 | 88 | 30 |
| 15 | 15.6 | 90 | 55 | 10 | 88 | 100 | 100 | 70 | 45 | 50 |
| 16 | 125 | 85 | 70 | 50 | 88 | 80 | 100 | 75 | 75 | 75 |
| 17 | 62.5 | 90 | 70 | 85 | 70 | 85 | 95 | 60 | 60 | 75 |

30. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 Kg/Ha is achieved when 50 mg of test compound is employed.

The treated pots and control pots were placed in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 3.

TABLE 3

PREEMERGENCE HERBICIDAL ACTIVITY

| Cpd. No. | Rate, Kg/Ha | Morning-glory | Pigweed | Velvet-leaf | Wild Buck-wheat | Black-grass | Barn-yard Grass | Johnson-grass |
|---|---|---|---|---|---|---|---|---|
| 1 | 1.12 | 50 | 100 | 80 | 60 | 50 | 30 | 40 |
| 2 | 0.28 | 50 | 98 | 80 | 50 | 60 | 30 | 0 |
| 3 | 0.56 | 50 | 98 | 50 | 80 | 100 | 80 | 80 |
| 4 | 2.24 | 98 | — | 90 | 20 | 60 | 85 | 90 |
| 5 | 2.24 | 20 | 95 | 30 | 0 | 20 | 60 | 90 |
| 6 | 0.28 | 50 | 100 | 80 | 65 | 60 | 80 | 90 |
| 7 | 0.28 | 75 | 90 | 75 | 75 | 60 | 90 | 90 |
| 9 | 0.56 | 50 | 100 | 50 | 70 | 90 | 98 | 85 |
| 10 | 2.24 | 0 | 98 | 40 | 40 | 40 | 60 | 0 |
| 12 | 0.14 | 60 | 100 | 80 | 70 | 100 | 98 | 75 |
| 13 | 0.14 | 80 | 90 | 75 | 90 | 50 | 90 | 80 |
| 14 | 0.14 | 90 | 100 | 50 | 95 | 99 | 20 | 20 |
| 15 | 0.28 | 90 | 100 | 85 | 90 | 5 | 50 | 50 |
| 16 | 1.12 | 80 | 95 | 75 | 75 | 98 | 20 | 85 |

What is claimed is:

1. A 5-alkoxy-N-aryl[1,2,4]triazolo[1,5-c]-pyrimidine-2-sulfonamide compound of the formula:

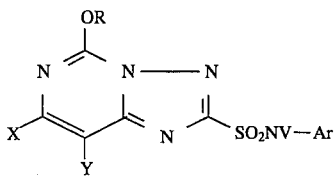

wherein

R represents $CH_2CF_3$ or $(C_1-C_3)$alkyl optionally monosubstituted with F, Cl, or $OCH_3$;

X and Y together represent a biradical fragment of the formula —Z—CH=CH—, —CH=CH—Z—, —Z—$CH_2$—$CH_2$—, —$CH_2$—$CH_2$—Z—, —$(CH_2)_3$—, —CH=CH—CH=CH—, or —N=CH—CH=CH— each optionally substituted with $CH_3$;

Z represents O, or S;

V represents H, COR', $CO_2R''$, or $CONR'''_2$;

Ar represents an aromatic moiety one of the formulas:

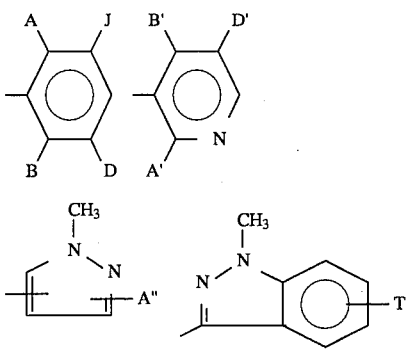

A represents F, Cl, Br, $CO_2R''$, $CONR'''_2$, $(C_1-C_2)$haloalkyl, $NO_2$, CN, SOR', or $SO_2R'$;

B represents H, $CH_3$, $C_2H_5$, F, Cl, Br, CN, OR', SR', $NR'''_2$, phenyl, or phenoxy, each phenyl and phenoxy optionally possessing 1 to 3 substituents selected from the group consisting of F, Cl, Br, CN, $CF_3$, $NO_2$, and $CH_3$;

D and J each independently represents H or $CH_3$ with the proviso that at least one of D and J represents H;

A' and B' each independently represents H, R', OR', $S(O)_nR'$, F, Cl, Br, I, CN, $NO_2$, $C_6H_5$, $CO_2R''$, or $CONR'''_2$ with the proviso that not more than one of A' and B' represents H;

D' represents H, F, Cl, Br, I, $CF_3$, or $CH_3$;

A" represents F, Cl, Br, I, $CF_3$, $SCF_3$, CN, $CO_2R''$, or $CONR'''_2$ and is located in the 4-position when the point of attachment is the 3- or 5-position and represents F, Cl, Br, I, $CF_3$, or $CH_3$ and is located in the 3- and/or 5-position when the point of attachment is the 4-position;

T represents H or F;

n represents 0, 1, or 2;

R' represents $(C_1-C_4)$alkyl optionally singly to completely substituted with fluorine;

R" represents $(C_1-C_4)$alkyl, $(C_3-C_4)$alkenyl, or $(C_3-C_4)$alkynyl;

R''' represents H or $(C_1-C_4)$alkyl; and when V represents H, the agriculturally acceptable salts thereof.

2. A compound according to claim 1 wherein V represents H.

3. A compound according to claim 1 wherein X and Y together represent the biradical —CH=CH—S— or —$(CH_2)_3$—.

4. A compound according to claim 1 wherein Ar represents substituted phenyl of the formula

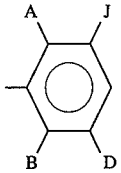

wherein A represents one of F, Cl, Br, $CO_2R''$, $NO_2$, and $CF_3$; B represents one of F, Cl, Br, $OCH_3$, and $CH_3$; J represents H, and D represents H or $CH_3$.

5. A compound according to claim 4 wherein A represents F, Cl or $CO_2CH_3$, B represents F or Cl, and D and J each represent H.

6. A compound according to claim 1 wherein Ar represents substituted 3-pyridinyl of the formula

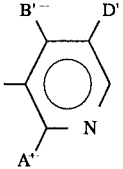

wherein A' represents Cl, F, or $OCH_3$; B' represents $CH_3$, $OCH_3$, $OC_2H_5$, $OC_3H_7$(n), or $OC_3H_7$(i); and D' represents H or wherein A' represents H, B' represents $CO_2(C_1-C_2)$alkyl and D' represents H.

7. A compound according to claim 1 wherein Ar represents substituted 3-, 4-, or 5-pyrazolyl of the formula:

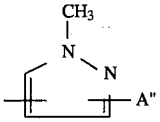

wherein A" represents Cl, Br, I, or $CF_3$.

8. An herbicidal composition comprising an herbicidally effective amount of a 5-alkoxy-N-aryl[1,2,4]triazolo[1,5-c]pyrimidine-2-sulfonamide compound of the formula:

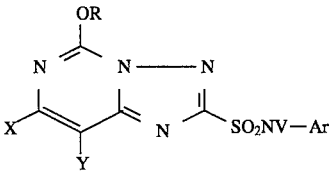

wherein

R represents $CH_2CF_3$ or $(C_1-C_3)$ alkyl optionally monosubstituted with F, Cl, or $OCH_3$;

X and Y together represent a biradical fragment of the formula —Z—CH=CH—, —CH=CH—Z—, —Z—$CH_2$—$CH_2$—, —$CH_2$—$CH_2$—Z—, —$(CH_2)_3$—, —CH=CH—CH=CH—, or —N=CH—CH=CH— each optionally substituted with $CH_3$;

Z represents O, or S;

V represents H, COR', $CO_2R''$, or $CONR'''_2$;

Ar represents an aromatic moiety one of the formulas:

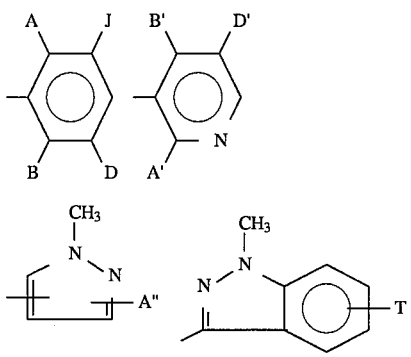

A represents F, Cl, Br, CO$_2$R'', CONR'''$_2$, (C$_1$–C$_2$)haloalkyl, NO$_2$, CN, SOR', or SO$_2$R';

B represents H, CH$_3$, C$_2$H$_5$, F, Cl, Br, CN, OR', SR', NR'''$_2$, phenyl, or phenoxy, each phenyl and phenoxy optionally possessing 1 to 3 substituents selected from the group consisting of F, Cl, Br, CN, CF$_3$, NO$_2$, and CH$_3$;

D and J each independently represents H or CH$_3$ with the proviso that at least one of D and J represents H;

A' and B' each independently represents H, R', OR', S(O)$_n$R', F, Cl, Br, I, CN, NO$_2$, C$_6$H$_5$, CO$_2$R'', or CONR'''$_2$ with the proviso that not more than one of A' and B' represents H;

D' represents H, F, Cl, Br, I, CF$_3$, or CH$_3$;

A'' represents F, Cl, Br, I, CF$_3$, SCF$_3$, CN, CO$_2$R'', or CONR'''$_2$ and is located in the 4-position when the point of attachment is the 3- or 5-position and represents F, Cl, Br, I, CF$_3$, or CH$_3$ and is located in the 3- and/or 5-position when the point of attachment is the 4-position;

T represents H or F;

n represents 0, 1, or 2;

R' represents (C$_1$–C$_4$)alkyl optionally singly to completely substituted with fluorine;

R'' represents (C$_1$–C$_4$)alkyl, (C$_3$–C$_4$)alkenyl, or (C$_3$–C$_4$)alkynyl;

R''' represents H or (C$_1$–C$_4$)alkyl; and when V represents H, the agriculturally acceptable salts thereof in admixture with an agriculturally acceptable adjuvant or carrier.

9. A composition according to claim 8 wherein V represents H.

10. A composition according to claim 8 wherein X and Y together represent the biradical —CH=CH—S— or —(CH$_2$)$_3$—.

11. A composition according to claim 8 wherein Ar represents substituted phenyl of the formula

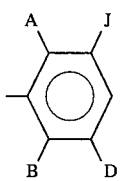

wherein A represents one of F, Cl, Br, CO$_2$R'', NO$_2$, and CF$_3$; B represents one of F, Cl, Br, OCH$_3$, and CH$_3$; J represents H, and D represents H or CH$_3$.

12. A composition according to claim 11 wherein A represents F, Cl, or CO$_2$CH$_3$, B represents F or Cl, and D and J each represent H.

13. A composition according to claim 8 wherein Ar represents substituted 3-pyridinyl of the formula

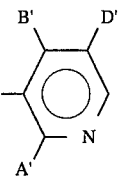

wherein A' represents Cl, F, or OCH$_3$; B' represents CH$_3$, OCH$_3$, OC$_2$H$_5$, OC$_3$H$_7$(n), or OC$_3$H$_7$(i); and D' represents H or wherein A' represents H, B' represents CO$_2$(C$_1$–C$_2$)alkyl and D' represents H.

14. A composition according to claim 8 wherein Ar represents substituted 3-, 4-, or 5-pyrazolyl of the formula:

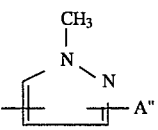

wherein A'' represents Cl, Br, I, or CF$_3$.

15. A method of controlling undesirable vegetation which comprises applying to said vegetation or to the locus thereof an herbicidally effective amount of a 5-alkoxy-N-aryl[1,2,4]triazolo[1,5-c]pyrimidine-2-sulfonamide compound of the formula:

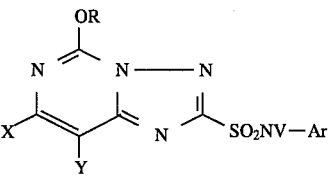

wherein

R represents CH$_2$CF$_3$ or (C$_1$–C$_3$) alkyl optionally monosubstituted with F, Cl, or OCH$_3$;

X and Y together represent a biradical fragment of the formula —Z—CH=CH—, —CH=CH—Z—, —Z—CH$_2$—CH$_2$—, —CH$_2$—CH$_2$—Z—, —(CH$_2$)$_3$—, —CH=CH—CH=CH—, or —N=CH—CH=CH— each optionally substituted with CH$_3$;

Z represents O, or S;

V represents H, COR', CO$_2$R'', or CONR'''$_2$;

Ar represents an aromatic moiety one of the formulas:

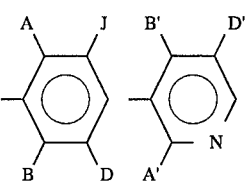

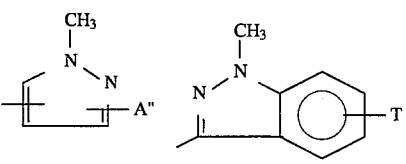

A represents F, Cl, Br, CO$_2$R'', CONR'''$_2$, (C$_1$–C$_2$)haloalkyl, NO$_2$, CN, SOR', or SO$_2$R';

B represents H, CH$_3$, C$_2$H$_5$, F, Cl, Br, CN, OR', SR', NR'''$_2$, phenyl, or phenoxy, each phenyl and phenoxy optionally possessing 1 to 3 substituents selected from the group consisting of F, Cl, Br, CN, CF$_3$, NO$_2$, and CH$_3$;

D and J each independently represents H or CH$_3$ with the proviso that at least one of D and J represents H;

A' and B' each independently represents H, R', OR', S(O)$_n$R', F, Cl, Br, I, CN, NO$_2$, C$_6$H$_5$, CO$_2$R", or CONR'''$_2$ with the proviso that not more than one of A' and B' represents H;

D' represents H, F, Cl, Br, I, CF$_3$, or CH$_3$;

A" represents F, Cl, Br, I, CF$_3$, SCF$_3$, CN, CO$_2$R", or CONR'''$_2$ and is located in the 4-position when the point of attachment is the 3- or 5-position and represents F, Cl, Br, I, CF$_3$, or CH$_3$ and is located in the 3- and/or 5-position when the point of attachment is the 4-position;

T represents H or F;

n represents 0, 1, or 2;

R' represents (C$_1$–C$_4$)alkyl optionally singly to completely substituted with fluorine;

R" represents (C$_1$–C$_4$)alkyl, (C$_3$–C$_4$) alkenyl, or (C$_3$–C$_4$) alkynyl;

R''' represents H or (C$_1$–C$_4$)alkyl; and when V represents H, the agriculturally acceptable salts thereof.

16. A method according to claim 15 wherein V represents H.

17. A method according to claim 15 wherein X and Y together represent the biradical —CH=CH—S— or —(CH$_2$)$_3$—.

18. A method according to claim 15 wherein Ar represents substituted phenyl of the formula

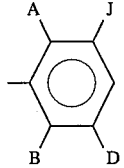

wherein A represents one of F, Cl, Br, CO$_2$R", NO$_2$, and CF$_3$; B represents one of F, Cl, Br, OCH$_3$, and CH$_3$; J represents H, and D represents H or CH$_3$.

19. A method according to claim 18 wherein A represents F, Cl, or CO$_2$CH$_3$, B represents F or Cl, and D and J each represent H.

20. A method according to claim 19 wherein Ar represents substituted 3-pyridinyl of the formula

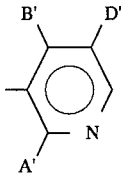

wherein A' represents Cl, F, or OCH$_3$; B' represents CH$_3$, OCH$_3$, OC$_2$H$_5$, OC$_3$H$_7$(n), or OC$_3$H$_7$(i); and D' represents H or wherein A' represents H, B' represents CO$_2$(C$_1$–C$_2$)alkyl and D' represents H.

21. A method according to claim 15 wherein Ar represents substituted 3-, 4-, or 5-pyrazolyl of the formula:

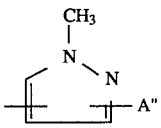

wherein A" represents Cl, Br, I, or CF$_3$.

22. A chlorosulfonyl compound of the formula:

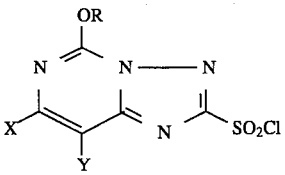

wherein

R represents Cl, CH$_2$CF$_3$ or (C$_1$–C$_3$)alkyl optionally monosubstituted with F, Cl, or OCH$_3$; and X and Y together represent the biradical —CH=CH—S— or —(CH$_2$)$_3$—.

* * * * *